United States Patent [19]

Borgarello et al.

[11] Patent Number: 4,942,179
[45] Date of Patent: Jul. 17, 1990

[54] SINGLE-PHASE COMPOSITION CONTAINING A PERFLUORINATED OIL AND ONE OR MORE SURFACTANT(S), USEFUL AS AN EXCIPIENT FOR COSMETIC AND DERMATOLOGIC FORMULATIONS, AS WELL AS FOR BIOMEDICAL APPLICATIONS

[75] Inventors: Enrico Borgarello, Turin; Filippo M. Carlini, Vicenza; Carlo Neri, San Donato Milanese; Edoardo Platone, Asti, all of Italy

[73] Assignees: Eniricherche S.p.A., Milan; Enichem Synthesis S.p.A., Palermo, both of Italy

[21] Appl. No.: 206,599

[22] Filed: Jun. 14, 1988

[30] Foreign Application Priority Data

Jun. 23, 1987 [IT] Italy ................. 20977 A/87
Jun. 23, 1987 [IT] Italy ................. 20998 A/87

[51] Int. Cl.$^5$ ................. A61K 31/13; A61K 31/535; A61K 31/445; A61K 31/35
[52] U.S. Cl. ................. 514/659; 514/231.2; 514/315; 514/451; 514/461; 514/661; 514/672; 514/715; 514/722; 514/747; 514/759; 514/772; 514/788; 514/832; 514/975
[58] Field of Search ............. 514/832, 451, 975, 461, 514/449, 659, 231.2, 315, 451, 461, 661, 672, 715, 722, 747, 759, 772, 788; 558/174, 186, 170

[56] References Cited

U.S. PATENT DOCUMENTS 3,094,547  6/1963  Heine ................. 558/175
4,105,798  8/1978  Moore et al. ................. 514/832

Primary Examiner—Douglas W. Robinson
Assistant Examiner—Zohreh A. Fay
Attorney, Agent, or Firm—Hedman, Gibson, Costigan & Hoare

[57] ABSTRACT

A single-phase, either isotropic or anisotropic formulation is disclosed, which contains perfluorinated oil and one or more surfactant(s), is useful as an excipient for cosmetic and dermatologic formulations and is characterized in that at least one surfactant is selected from those having the following general formula:

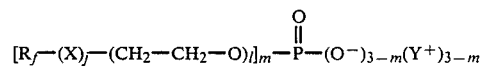

wherein:
$R_F$ is an $F-(CF_2-CF_2)_i-$ group;
X is a group selected from:

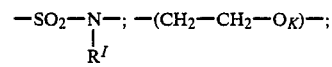

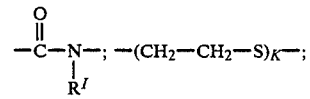

$-(CH_2-O)_K-$; and $-(CH_2-S)_K-$; wherein $R^I$ is a $(C_1-C_4)$-alkyl;
Y is a group selected from: $NH_2(R^{II})_2$ and $N(R^{II})_4$; wherein $R^{II}$ is a hydrogen atom, or a group selected from $-CH_2-CH_2-OH$ and $(C_1-C_4)$-alkyl;
i is an integer comprised within the range of from 3 to 8;
j is zero or 1;
K is 2.1;
l is an integer comprised within the range of from 1 to 10;
m is 1 or 2.

Such composition is spontaneously formed when the components are simply placed into contact with one another.

In particular, in case of the isotropic form, the composition is a fluid, clear and stable composition, with particle size smaller than 400 Å, containing:
(a) from 1 to 50% by weight of the perfluorinated oil;
(b) from 1 to 50% by weight of water;
(c) from 8 to 60% by weight of at least one surfactant selected from the above defined surfactants;
(d) from 6 to 38% by weight of a co-surfactant, selected from $(C_3-C_7)$-aliphatic alcohols.

In case of the anisotropic form, the composition has a high viscosity, and contains:
(a) from 1 to 50% by weight of the perfluorinated oil;
(b) from 1 to 80% by weight of water;
(c) from 1 to 40% by weight of at least one surfactant selected from the above defined surfactants;
(d) from 0 to 19% by weight of a co-surfactant, selected from $(C_3-C_7)$-aliphatic alcohols.

Furthermore, in case of the isotropic composition this latter finds use also in the biomedical sector.

15 Claims, No Drawings

SINGLE-PHASE COMPOSITION CONTAINING A PERFLUORINATED OIL AND ONE OR MORE SURFACTANT(S), USEFUL AS AN EXCIPIENT FOR COSMETIC AND DERMATOLOGIC FORMULATIONS, AS WELL AS FOR BIOMEDICAL APPLICATIONS

The present invention relates to a single-phase, isotropic fluid, or anisotropic composition containing a perfluorinated oil and a special surfactant defined in the following.

The same invention relates as well to the use of such composition as an excipient for cosmetic and dermatologic formulations and, in case of the isotropic form, in the biomedical sector.

In the art, emulsions of oil-in-water type are known, in which the oil is constituted by a perfluorinated organic compound (a perfluorinated oil), such as perfluorinated alkanes or cycloalkanes, perfluorinated amines and perfluorinated polyethers.

These emulsions have been used for cosmetic or dermatologic formulations, wherein their ability to form gas-permeable films is taken advantage of, such as disclosed, e.g., in European patent application publ. No. 196,904.

Furthermore, some emulsions were prepared in order to have available substitutes for blood (artificial blood), wherein the solubility of oxygen and carbon dioxide in the perfluorinated oils is exploited, with the perfluorinated oils therefore performing the function of oxygen transport, such as disclosed, e.g., in U.S. Pat. No. 4,325,972. This use is also reported in the "Proceedings of the $3^{rd}$ Congress of International Conference on Blood Substitutes" Montreal (Canada), June 26–28 (1987).

In the art, also gels are known, which are capable of transporting gases, such as, e.g., those disclosed in U.K. patent application No. 2,087,882. These gels are obtained by emulsifying a mixture containing water, a perfluorinated oil and a surfactant agent, concentrating the emulsion in order to form a gel phase and a liquid phase, and separating the two so-formed phases. The so obtained gel is used, inter alia, as an ointment, or a cosmetic.

The preparation of these emulsions can be affected by problems deriving from the selection of an efficacious emulsifier, and from the stability of the same emulsions. In any case, said preparation requires large amounts of energy, in that these emulsions are formed by sonication, or by homogenization under high pressure, by means of a shear effect.

In the art, also some microemulsions containing perfluorinated oils were described, which are capable of forming spontaneously, such as, e.g., those described by E. Ceschin et al. in J. Chem. Techn. Biotechnol., 35A 73 (1985) and by G. Mathis et al. in J. Am. Chem. Soc., 1984, 106, 6162 and in French patent No. 2,515,198.

These microemulsions known from the prior art, if on one hand overcome the problems deriving from the expenditure of energy necessary for them being formed, show, on the other hand, some problems.

First of all, no surfactants were found in the prior art, which would be capable of showing their efficacy when they are combined with the various perfluorinated oils known in the art. Therefore, resort was had to surfactants specific for the individual perfluorinated oils, or to mixtures of a plurality of surfactants. Furthermore, the content of perfluorinated oil in such compositions is generally low, so that the same microemulsions represent relatively poorly interesting vehicles for oxygen transport. Finally, not always the size of the particles in said microemulsions is comprised within a desired range of values.

The purpose of the present invention is overcoming the above outlined drawbacks of the prior art.

According to the present invention, it was found that a single-phase composition can be directly obtained, with their formation occurring spontaneously, by starting from practically any known perfluorinated oils, by using surfactants belonging to a particular class. The single-phase composition of the present invention can either be, according to the percentages of the various constituents and the size of the particles, as specified hereinunder, isotropic, transparent and fluid, or it can be an anisotropic, high-viscosity formulation.

By the term "anisotropic, single-phase composition", according to the present invention a homogeneous system is meant, which is constituted by perfluorinated oil, water, surfactant, and optionally co-surfactant, freely flowing, having a viscosity higher than 100 cstokes, showing three-dimensional non-continuous structures, as shown by measurements on optical microscope under polarized light.

By the term "isotropic, single-phase composition", according to the present invention a homogeneous system is meant, which is constituted by perfluorinated oil, water, surfactant, and co-surfactant, fluid, having a viscosity comprised within the range of from 1 to 50 cstokes, showing a three-dimensional continuous structure, as shown by measurements on optical microscope under polarized light.

Said isotropic composition is endowed with characteristics of high stability to temperature and oxygen pressure, even at high concentrations of the perfluorinated oil, and is therefore useful in the application in the cosmetic sector, in the dermatologic sector (as the previous one), in the sector of blood substitutes, and in the biomedical sector in general.

According to as hereinabove stated, the present invention relates therefore to a single-phase composition based on a perfluorinated oil, containing one or more surfactant(s), wherein at least one of said surfactant(s) is equal to at least one of the surfactants having the following general formula:

$$[R_F-(X)_j-(CH_2-CH_2-O)_l]_m-\overset{O}{\underset{\|}{P}}-(O^-)_{3-m}(Y^+)_{3-m} \quad (I)$$

wherein:

$R_F$ is an $F-(CF_2-CF_2)_i-$ group X is a group selected from:

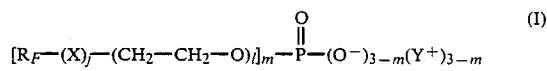

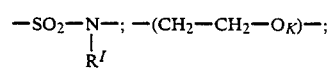

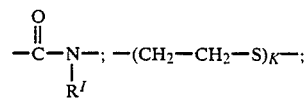

$-(CH_2-O)_K-$; and $-(CH_2-S)_K-$; wherein $R^I$ is a $(C_1-C_4)$-alkyl;

Y is a group selected from: $NH_2(R^{II})_2$ and $N(R^{II})_4$; wherein $R^{II}$ is a hydrogen atom, or a group selected from —$CH_2$—$CH_2$—OH and $(C_1-C_4)$-alkyl;

i is an integer comprised within the range of from 3 to 8;

j is zero or 1;

K is 2 l;

l is an integer comprised within the range of from 1 to 10;

m is 1 or 2.

In case of the isotropic form, the above-said single-phase composition is furthermore a fluid and transparent composition having a viscosity comprised within the range of from 1 to 50 cstokes, with particle size smaller than 400 Å, and containing:

(a) from 1 to 50% by weight of the perfluorinated oil;
(b) from 1 to 50% by weight of water;
(c) from 8 to 60% by weight of at least one surfactant selected from the surfactants having the above formula (I);
(d) from 6 to 38% by weight of a co-surfactant, selected from $(C_3-C_7)$-liphatic alcohols.

In the preferred form of practical embodiment, the isotropic, single-phase composition according to the present invention comprises:

15–35% by weight of the (a) component;
30–50% by weight of the (b) component;
8–20% by weight of the (c) component;
6–15% by weight of the (d) component;

the particle size in said composition being comprised within the range of from 50–200 Å.

In the particular case of the anisotropic single-phase form, the composition has a viscosity higher than 100 cstokes, with a particle size larger than 1 micron, and contains:

(a) from 1 to 50% by weight of perfluorinated oil;
(b) from 1 to 80% by weight of water;
(c) from 1 to 40% by weight of at least one surfactant selected from the surfactants defined by means of the general formula (I);
(d) from 0 to 19% by weight of a co-surfactant, selected from $(C_3-C_7)$-aliphatic alcohols.

In the preferred form of practical embodiment, the anisotropic, single-phase composition according to the present invention comprises:

20–45% by weight of the (a) component;
45–70% by weight of the (b) component;
3–12% by weight of the (c) component; and
0–8% by weight of the (d) component;

the particle size in said composition being larger than 1 micron, and the viscosity of said composition being higher than 100 cstokes.

The perfuorinated oils useful for the purposes of the present invention are those known in the art, and generally belonging to the following classes of compounds: perfluorinated alkanes and cycloalkanes; perfluorinated amines; non-cyclic or cyclic perfluorinated ethers; and perfluorinated heterocyclic compounds.

Examples of perfluorinated alkanes are perfluoro-heptane and perfluoro-octane.

Examples of perfluorinated cycloalkanes are perfluoro-alkyl-cyclohexanes, containing from 1 to 3 carbon atoms in their alkyl group; (cis and trans) perfluorodecalin; and perfluoro-alkyl-decalins containing from 1 to 3 carbon atoms in the alkyl group.

Examples of perfluorinated amines are perfluorinated aliphatic amines and perfluorinated alicyclic amines, such as perfluoro-tripropyl-amine; perfluoro-tributyla-mine; perfluoro-triamyl-amine and perfluoro-N,N-dialkylcyclohexyl-amines, wherein the alkyl group contains from 1 to 6 carbon atoms. Examples of perfluoro-N,N-dialkylcyclohexyl-amines are perfluoro-N,N-dimethyl-cyclohexylamine; perfluoro-N,N-diethyl-cyclohexyl-amine; and perfluoro-N,N-dibutyl-cyclohexyl-amine.

Examples of perfluoroethers are perfluoro-alkyl-tetrahydrofuran and perfluoro-alkyl-tetrahydropyran, containing from 1 to 7 carbon atoms in their alkyl group, and the products available from the market under the following trade names:

FOMBLIN® (e.g.,: FOMBLIN® Y04, Y25 and YR) by Montefluos;

GALDEM® (e.g.,: GALDEM® ME) by MONTE-FLUOS;

FR-80® by 3M; and

RM 101® by Enichem Sintesi.

Examples of perfluorinated heterocyclic compounds are perfluoroalkyl-piperidines and pefluoroalkylmorpholines, wherein the alkyl group contains from 1 to 7 carbon atoms.

Mixtures of two or more perfluornated oils can be used.

A preferred surfactant for the purposes of the present invention can be defined by means of the following formula (II):

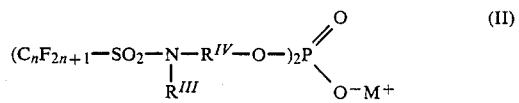

wherein:

n is an integer comprised within the range of from 3 to 10;

$R^{III}$ is a $(C_1-C_3)$-alkyl;

$R^{IV}$ is a $(C_1-C_3)$-alkylene;

$M^+$ is ammonium ion.

A very preferred surfactant for the purposes of the present invention is the one as defined by above formula (II), wherein:

n is 8;

$R^{III}$ is ethyl;

$R^{IV}$ is ethylidene; and $M^+$ is ammonium ion.

The monoester/diester mixture, with monoester/diester percentages comprised within the range of from 0–50% to 100–50% can be used as well.

The preferred co-surfactant is isopropanol.

The anisotropic single-phase composition of the present invention is spontaneously formed when the components are simply contacted with one another, by operating at room temperature (20°–25° C.), or at higher than room temperatures, up to approximately 50° C., as a function of the nature of the perfluorinated oil used, in particular of its vapour pressure. The modalities and the order of contact of the components are not critical.

The anisotropic single-phase composition of the present invention is endowed with characteristics of high stability to temperature, to oxygen pressure and to the storage under normal room conditions.

Said composition can be formulated into creams for cosmetic and dermatologic use, which have a high film-forming and coating power, a strong hydrophobic character, and absolute absence of toxicity and a strong ability to dissolve oxygen and to supply oxygen to tissues. In particular, creams for hand care, for sun shielding, for protection from cold, for the management of burns, for anti-wrinkle treatment, and the like, can be obtained. The active agents, useful for the intended purpose, are those as normally used in the art, including the materials of proteinic nature.

The process of preparation of the creams is advantageously carried out by dissolving the water-soluble active principles in the aqueous phase, and then placing said aqueous phase in contact with the perfluorinated oil, in which the oil-soluble active principles have been previously dissolved.

Also the isotropic, single-phase composition of the present invention spontaneously forms when the components are simply contacted with one another, by operating at room temperature (20°-25° C.) or at temperatures close to room temperatures.

As in the previous case, the modalities of contact of components are not critical, but, according to a preferred form of practical embodiment, the perfluorinated oil is placed into contact with an aqueous solution of the surfactant and of the co-surfactant.

The isotropy of the composition according to the present invention can be verified by observation on optical microscope under polarized light, and by means of centrifugation, rheologic and turbidimetric measurements.

The isotropic single-phase composition of the present invention is endowed with characteristics of high temperature stability, stability to oxygen pressure and to storage, as it will clearly result from the hereinunder reported experimental examples.

Said isotropic, single-phase composition is useful in the cosmetic and dermatologic sector, in the sector of blood substitutes, and in the biomedical sector in general.

Specific examples of sectors of use of the compositions according to the present invention are: perfusion of transplated organs; extracorporeal circulation in surgery; management of cardiovascular infarction and of cerebral ischemia; cardioplegy; oxygenation of cerebral tissues; blood-less surgery; radiotherapy of tumors and assistance in chemotherapy; therapy for carbon-monoxide poisoning; blood substitute in hemorrhages and anemias; X rays on human body; NMR for investigation into human body; transport of drugs; retinal treatments and management of emboli.

In particular, a blood substitute can be prepared by first forming an aqueous solution containing the surfactant, the co-surfactant, the salts, the metabolites and other biologically-important compounds. To the so-obtained solution, the perfluorinated oil is added in order to cause an isotropic single-phase composition to spontaneously form.

In the preparation of the cosmetic or dermatologic compositions, the process is carried out like in case of the anisotropic composition.

The following experimental examples are illustrative and non-limitative of the purview of the present invention.

EXAMPLE 1

(a) Test

As the perfluorinated oil, the commercial product RM 101 ® by Enichem Sintesi is used.

RM 101 ® is a mixture of perfluoroethers containing 55.6% by weight of perfluoro-1-n.butyl-tetrahydrofuran:

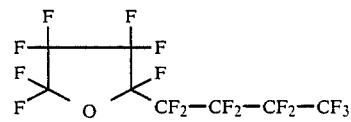
(III)

and 18.5% by weight of perfluoro-1-n.propyltetrahydropyran:

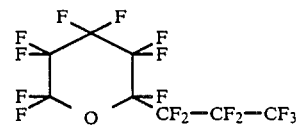
(IV)

with the balance to 100% being constituted by isomers of compounds (III) and (IV).

0.3488 g is prepared of an aqueous solution containing 0.043 g of isopropanol and 0.1046 g of the surfactant represented by formula (II), in which:
is 8,
R is ethyl,
$R^I$ is ethylidene, and
$M^+$ is ammonium ion.

This solution is added to 0.3562 g of perfluorinated oil RM 101 ®, by operating at room temperature (20°-25° C.).

An isotropic single-phase, transparent composition forms, which has a viscosity of 20 cts (centistokes) and contains, as percentages by weight:

| | |
|---|---|
| RM 101 ® | 34% |
| Surfactant | 10% |
| Isopropanol | 7% |
| Water | 49% |

(b) Test

To 0.9164 g of RM 101 ®, 2.3982 g of an aqueous solution containing 0.7194 of the same surfactant as of the (a) Test, and 0.5036 g of isopropanol is added. 0.229 g of water is then added. All operations are carried out at room temperature.

An isotropic single-phase and transparent composition is obtained, which has a viscosity of approximately 10 cts, and contains, as percentages by weight:

| | |
|---|---|
| RM 101 ® | 29.5% |
| Surfactant | 20.3% |
| Isopropanol | 14.2% |
| Water | 39.6% |

The so-obtained composition is submitted to the following treatments: 48 hours at 0° C., then heating to 80° C. and standing at this temperature for 24 hours.

This treatment is repeated a plurality of times, with the characteristics of the composition not undergoing any alterations, as determined by observation on optical microscope under polarized light.

Furthermore, the composition remains unchanged after a treatment of centrifugation at 100 G for 10 minutes. Finally, the composition maintains its characteristics of isotropy, single-phase nature, fluidity and transparency unchanged after a one-month storage under room conditions.

(c) Test

To 0.8694 g of an aqueous solution containing 0.2602 g of the same surfactant as of the (a) Test and 0.1826 g of isopropanol, 0.3203 g of RM 101 ® is added, by operating at room temperature.

An isotropic single-phase and transparent composition is obtained, which contains, as percentages by weight:

| | |
|---|---|
| RM 101 ® | 26.9% |
| Surfactant | 21.8% |
| Isopropanol | 15.5% |
| Water | 35.8% |

To the so-obtained composition, 0.4509 g of RM 101 ® and 0.2462 g of water are added by operating at room temperature, and an isotropic single-phase and transparent composition is obtained, which contains, as percentages by weight:

| | |
|---|---|
| RM 101 ® | 40.9% |
| Surfactant | 13.7% |
| Isopropanol | 9.8% |
| Water | 35.6% |

By means of successive additions of RM 101 ® and of water, the formation of a gel, and of an emulsion is caused, and then a phase separation is reached.

(d) Test

To 0.7597 g of an aqueous solution containing 0.2260 g of the same surfactant as of the (a) Test and 0.1615 g of isopropanol, 0.2227 g of water is added. An anisotropic system is obtained, with liquid crystals being formed. To this system, 0.2911 g of RM 101 ® is added. All operations are carried out by operating at room temperature.

An isotropic single-phase, transparent and fluid composition is obtained, which contains, as percentages by weight:

| | |
|---|---|
| RM 101 ® | 22.8% |
| Surfactant | 17.8% |
| Isopropanol | 12.7% |
| Water | 46.7% |

(e) Test 0.3578 g of the same surfactant as of the (a) Test is weighed and is added to 0.2570 g of isopropanol, and 0.4389 g of water. An isotropic, transparent and fluid solution is obtained.

To such a solution, 0.1390 g of RM 101 ® is added. All operations are carried out at room temperature.

An isotropic single-phase, transparent and fluid composition is obtained, which contains, as percentages by weight:

| | |
|---|---|
| RM 101 ® | 11.6% |
| Surfactant | 29.2% |
| Isopropanol | 22.5% |
| Water | 36.7% |

(f) Test 0.2330 g of the same surfactant as of the (a) Test is weighed and 0.1800 g of isopropanol, and 0.1172 g of water are added. An isotropic and transparent solution is obtained.

To such a solution, 0.1386 g of RM 101 ® is added. All operations are carried out at room temperature.

An isotropic single-phase, transparent and fluid composition is obtained, which contains, by weight:

| | |
|---|---|
| RM 101 ® | 20.8% |
| Surfactant | 36% |
| Isopropanol | 25.7% |
| Water | 17.5% |

EXAMPLE 2

Effect of isopropanol concentration on the compositions containing RM 101 ®, water and the same surfactant as of the (a) Test of Example 1.

In this Example, all operations are carried out at room temperature.

(a) Test

To 0.0689 g of the surfactant, 0.0924 g of water is added. An anisotropic, high-viscosity, single-phase system is formed. To such a system, 0.3451 g of RM 101 ® is added, in the form of a plurality of successive aliquots.

At the end of the addition, an anisotropic, single-phase and fluid composition is obtained.

(b) Test

To 0.1256 g of surfactant, 0.5744 g of RM 101 ® is added, and an anisotropic, high-viscosity and single-phase system is obtained. By adding 2.2484 g of water, an anisotropic, single-phase, fluid composition is formed.

(c) Test

To 0.5007 g of an aqueous solution of the surfactant, containing 0.1502 g of surfactant, 0.1052 g of isopropanol and 0.2453 g of water; 0.0666 g of isopropanol is added. An anisotropic single-phase, fluid and transparent system is obtained. To this system, 0.0682 g of RM 101 ® is then added, and an isotropic single-phase, transparent and fluid composition is obtained, which contains, as percentages by weight:

| | |
|---|---|
| RM 101 ® | 10.7% |
| Surfactant | 23.6% |
| Isopropanol | 27.1% |
| Water | 38.6% |

EXAMPLE 3

To 0.8577 g of an aqueous solution of the same surfactant as of Example 1, (a) Test, containing 0.2552 g of surfactant, 0.1822 g of isopropanol and 0.4203 g of water; 0.4313 g of perfluoro-trans-decalin is added. An anisotropic single-phase, fluid and transparent system is obtained, which contains, as percentages by weight:

| | |
|---|---|
| Perfluoro-trans-decalin | 33.5% |
| Surfactant | 19.8% |

-continued

|  |  |
|---|---|
| Isopropanol | 14.1% |
| Water | 32.6% |

EXAMPLE 4

To 1.1810 g of an aqueous solution of the same surfactant as of Example 1, (a) Test, containing 0.3513 g of surfactant, 0.2540 g of isopropanol and 0.5787 g of water, 0.5787 g of water is added, 0.1050 g of the commercial perfluoro-ether Galdem ® ME by Montefluos is added.

An isotropic single-phase, fluid and transparent composition is obtained, which contains, as percentages by weight:

|  |  |
|---|---|
| Galdem ® ME | 8.2% |
| Surfactant | 27.3% |
| Isopropanol | 19.5% |
| Water | 45% |

EXAMPLE 5

To 0.7480 g of an aqueous solution of the same surfactant as of Example 1, (a) Test, containing 0.2225 g of surfactant, 0.1590 g of isopropanol and 0.3665 g of water; 0.4421 g of perfluoro-methyl-morpholine is added.

An isotropic single-phase, fluid and transparent composition is obtained, which contains, as percentages by weight:

|  |  |
|---|---|
| perfluoro-methyl-morpholine | 32.7% |
| Surfactant | 17.8% |
| Isopropanol | 13.3% |
| Water | 30.8% |

EXAMPLE 6

To 0.5732 g of an aqueous solution of the same surfactant as of Example 1, (a) Test, containing 0.1696 g of surfactant, 0.1213 g of isopropanol and 0.2793 g of water; 0.0895 g of perfluoro-N,N-tributyl-amine (RM 175 ®, a commercial product by Enichem Sintesi) is added.

An isotropic single-phase, fluid and transparent system is obtained, which contains, as percentages by weight:

|  |  |
|---|---|
| perfluoro-N,N-tributyl-amine | 14% |
| Surfactant | 25.7% |
| Isopropanol | 18.3% |
| Water | 42% |

EXAMPLE 7

To 0.7448 g of an aqueous solution of the same surfactant as of Example 1, (a) Test, containing 0.2216 g of surfactant, 0.1582 g of isopropanol and 0.3650 g of water; 0.0571 g of perfluoro-N,N-tripentyl-amine (RM 200 ®, a commercial product by Enichem Sintesi) is added.

An isotropic single-phase, fluid and transparent composition is obtained, which contains, as percentages by weight:

|  |  |
|---|---|
| perfluoro-N,N-tripentyl-amine | 7.1% |
| Surfactant | 27.6% |
| Isopropanol | 19.8% |
| Water | 45.5% |

EXAMPLE 8

To 1.4516 g of an aqueous solution of the same surfactant as of Example 1, (a) Test, containing 0.4318 g of surfactant, 0.3085 g of isopropanol and 0.7113 g of water; 0.1702 g of perfluoro-ethyl-cyclohexylamine is added.

An isotropic single-phase, fluid and transparent composition is obtained, which contains, as percentages by weight:

|  |  |
|---|---|
| perfluoro-ethyl-cyclohexylamine | 10.5% |
| Surfactant | 26.6% |
| Isopropanol | 19% |
| Water | 43.9% |

EXAMPLE 9

Effect of oxygen pressure on the composition

To 1.0305 g of RM 101 ®, 2.5070 g of an aqueous solution of the same surfactant as of Example 1, (a) Test, containing 0.7521 g of surfactant, 0.5266 g of isopropanol and 1.2283 g of water, is added. Subsequently, 0.2020 g of water is added. The mixing is carried out at room temperature, under an oxygen pressure of 3 atm.

An isotropic single-phase, fluid and transparent composition is obtained, which contains, as percentages by weight:

|  |  |
|---|---|
| RM 101 ® | 27.7% |
| Surfactant | 20.1% |
| Isopropanol | 14.1% |
| Water | 38.1% |

EXAMPLE 10

Effect of the salts on the stability of the composition.

100 g of water is weighed. 0.381 g of NaCl, 0.226 g of KCl, 0.0465 g of $MgCl_2$, 0.070 g of $CaCl_2$ and 0.069 g of $NaH_2PO_4$ is added, and the pH value of the resulting solution is adjusted at 7.0 by means of the addition of $Na_2CO_3$.

To 0.9020 g of RM 101 ®, 2.3020 g of an aqueous solution of the same surfactant as of Example 1, (a) Test, containing 0.6906 g of surfactant, 0.4834 g of isopropanol and 1.1280 g of water is added. Subsequently, 0.220 g of the saline solution prepared as disclosed at the beginning of the present Example is added. The operations are carried out at room temperature.

An isotropic single-phase, fluid and transparent composition is obtained, which contains, as percentages by weight:

|  |  |
|---|---|
| RM 101 ® | 26.3% |
| Surfactant | 20.2% |
| Isopropanol | 14.1% |
| Saline solution | 39.4% |

EXAMPLE 11

As the perfluorinated oil, the commercial product RM 101 ® by Enichem Sintesi is used.

RM 101 ® is a mixture of perfluoroethers containing 55.6% by weight of perfluoro-1-n.butyl-tetrahydrofuran:

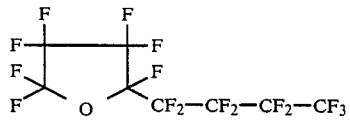 (III)

and 18.5% by weight of perfluoro-1-n.propyletrahydropyran:

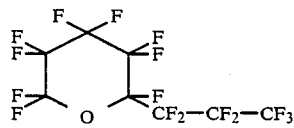 (IV)

with the balance to 100% being constituted by isomers of compounds (III) and (IV).

The same surfactant as represented by formula (II) is used, in which:
n is 8,
R is ethyl,
$R^I$ is ethylidene, and
$M^+$ is ammonium ion.

By operating at room temperature (20°–25° C.), to 0.0689 g of the surfactant, 0.0924 g of water and 0.0269 g of RM 101 ® are added An anisotropic single-phase, high-viscosity composition spontaneously forms, which contains, as percentages by weight:

| RM 101 ® | 14% |
|---|---|
| Surfactant | 36.6% |
| Water | 49.4% |

EXAMPLE 12

To 0.1256 g of the same surfactant as disclosed in Example 11, 0.5744 g of RM 101 ® and 0.5533 g of water are added.

The process is carried out at room temperature, and an anisotropic single-phase, high-viscosity composition spontaneously forms, which contains, as percentages by weight:

| RM 101 ® | 45.8% |
|---|---|
| Surfactant | 10% |
| Water | 44.2% |

EXAMPLE 13

To 5.0200 g of RM 101 ®, 1.4029 g of the same surfactant as disclosed in Example 11, 0.9814 g of isopropanol, and 7.665 g of water are added.

The process is carried out at room temperature, and an anisotropic single-phase, high-viscosity composition is obtained, which contains, as percentages by weight:

| RM 101 ® | 33.3% |
|---|---|
| Surfactant | 9.3% |
| Isopropanol | 6.5% |
| Water | 50.9% |

EXAMPLE 14

To 0.9412 g of RM 101 ®, 0.3788 g of the same surfactant as disclosed in Example 11, 0.2651 g of isopropanol, and 2.131 g of water are added.

The process is carried out at room temperature, and an anisotropic single-phase, high-viscosity composition is obtained, which contains, as percentages by weight:

| RM 101 ® | 18.6% |
|---|---|
| Surfactant | 7.5% |
| Isopropanol | 5.2% |
| Water | 68.7% |

EXAMPLE 15

To 0.4434 g of a mixture of the same surfactant as disclosed in Example 11 and isopropanol (0.2586 g of surfactant and 0.1848 of isopropanol), 1.3532 g of water and 1.1038 g of RM 101 ® are added.

The process is carried out at room temperature, and an anisotropic single-phase, high-viscosity composition is obtained, which contains, as percentages by weight:

| RM 101 ® | 38% |
|---|---|
| Surfactant | 8.9% |
| Isopropanol | 6.4% |
| Water | 46.7% |

We claim:

1. A spontaneously formed single-phase composition useful as an excipient in cosmetic, dermatologic, and biomedical applications, having isotropic or anisotropic forms, the composition comprising:
   (a) a perfluorinated oil;
   (b) water; and
   (c) a surfactant having the formula:

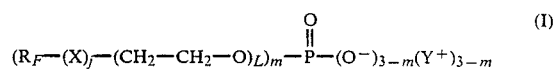 (I)

wherein,
$R_F$ is a $F-(CF_2-CF_2)_i-$ group,
X is a group selected from:

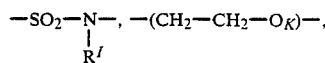

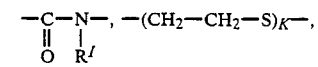

$-(CH_2-O)_K-$, and $-(CH_2-S)_K-$, wherein $R^I$ is a $(C_1-C_4)$-alkyl,
Y is a group selected from: $NH_2(R^{II})_2$ and $N(R^{II})_4$, wherein $R^{II}$ is a hydrogen atom, or a group selected from $-CH_2-CH_2-OH$ and $(C_1-C_4)$-alkyl,
i is an integer from 3 to 8,
j is zero or 1,
K is 2.L, L is an integer from 1 to 10, and m is 1 or 2.

2. The composition according to claim 1, wherein the composition is isotropic, fluid, has a viscosity of from 1 to 50 cstokes, has a particle size smaller than 400 Å, and comprises:
- (a) from 1 to 50% by weight of the perfluorinated oil;
- (b) from 1 to 50% by weight of the water;
- (c) from 8 to 60% by weight of the surfactant; and
- (d) from 6 to 38% by weight of a co-surfactant, selected from ($C_3$–$C_7$)-aliphatic alcohols.

3. The composition according to claim 2, wherein the particle size is from 50–200 Å and the composition comprises:
- (a) 15–35% by weight of the perfluorinated oil;
- (b) 30–50% by weight of the water;
- (c) 8–20% by weight of the surfactant; and
- (d) 6–15% by weight of a co-surfactant.

4. The composition according to claim 1, wherein the composition is anisotropic, has a viscosity higher than 100 cstokes, with a particle size larger than 1 micron, and comprises:
- (a) from 1 to 50% by weight of the perfluorinated oil;
- (b) from 1 to 80% by weight of the water;
- (c) from 1 to 40% by weight of the surfactant; and
- (d) from 0 to 19% by weight of a co-surfactant, selected from ($C_3$–$C_7$)-aliphatic alcohols.

5. The composition according to claim 4, comprising:
- (a) 20–45% by weight of the perfluorinated oil;
- (b) 45–70% by weight of the water;
- (c) 3–12% by weight of the surfactant; and
- (d) 0–8% by weight of the co-surfactant.

6. The composition according to claim 1, wherein the perfluorinated oil is selected from the group consisting of: perfluorinated alkanes and cycloalkanes, perfluorinated amines, non-cyclic or cyclic perfluorinated ethers, and perfluorinated heterocyclic compounds.

7. The composition according to claim 6, wherein the perfluorinated oil is selected from the group consisting of: perfluoro-heptane, perfluoro-octane, perfluoroalkyl-cyclohexanes containing from 1 to 3 carbon atoms in their alkyl group, perfluorodecalin, perfluoro-alkyl-decalins containing from 1 to 3 carbon atoms in their alkyl group, perfluoro-tripropyl-amine, perfluoro-tributyl-amine, perfluoro-triamyl-amine, perfluoro-N,N-dialkyl-cyclohexyl-amines containing from 1 to 6 carbon atoms in their alkyl group, perfluoro-alkyl-tetrahydrofurans containing from 1 to 7 carbon atoms in their alkyl group, perfluoro-alkyl-tetrahydropyrans containing from 1 to 7 carbon atoms in their alkyl group, perfluoroalkyl-piperidines containing from 1 to 7 carbon atoms in their alkyl group, perfluoroalkylmorpholines containing from 1 to 7 carbon atoms in their alkyl group, and mixtures of the foregoing.

8. The composition according to claim 1, wherein the surfactant is of the formula:

$$(C_nF_{2n+1}-SO_2-N(R^{III})-R^{IV}-O-)_2P(=O)(O^-M^+) \quad (II)$$

wherein, n is an integer from 3 to 10, $R^{III}$ is a ($C_1$–$C_3$)-alkyl, $R^{IV}$ is a ($C_1$–$C_3$)-alkylene, and $M^+$ is ammonium ion.

9. The composition according to claim 8, wherein:

n is 8, $R^{III}$ is ethyl, $R^{IV}$ is ethylidene, and $M^+$ is ammonium ion.

10. The composition according to claim 2 or 4, wherein the co-surfactant is isopropyl alcohol.

11. A method comprising formulating the composition according to claim 1 into creams for cosmetic and dermatologic applications.

12. A method comprising formulating the composition according to claim 1 into compositions for biomedical applications.

13. A process to produce a composition according to claim 1 comprising: blending the perfluorinated oil, the water, and the surfactant, the composition forming spontaneously by the blending of the reactants.

14. The process according to claim 13 to produce the composition in fluid, isotropic form, having a viscosity of from 1 to 50 cstokes, a particle size smaller than 400 Å, the process comprising: blending together from 1 to 50% by weight of the perfluorinated oil, from 1 to 50% by weight of the water, from 8 to 60% by weight of the surfactant, and from 6 to 38% by weight of a co-surfactant, selected from ($C_3$–$C_7$)-aliphatic alcohols.

15. The process according to claim 13 to produce the composition in anisotropic form, having a viscosity higher than 100 cstokes, a particle size larger than 1 micron, the process comprising: blending together from 1 to 50% by weight of the perfluorinated oil, from 1 to 80% by weight of the water, from 1 to 40% by weight of the surfactant, and from 0 to 19% by weight of a co-surfactant, selected from ($C_3$–$C_7$)-aliphatic alcohols.

* * * * *

UNITED STATES PATENT AND TRADEMARK OFFICE
CERTIFICATE OF CORRECTION

PATENT NO. : 4,942,179
DATED : July 17, 1990
INVENTOR(S) : Enrico Bogarello, et al.

It is certified that error appears in the above—identified patent and that said Letters Patent is hereby corrected as shown below:

On the title page, item [73]:
Assignees, line 1 delete "Enricherche" and insert --Eniricerche--

Signed and Sealed this

Twenty-ninth Day of October, 1991

Attest:

HARRY F. MANBECK, JR.

*Attesting Officer*    *Commissioner of Patents and Trademarks*